United States Patent
Li et al.

(10) Patent No.: US 9,630,939 B2
(45) Date of Patent: Apr. 25, 2017

(54) DERIVATIVE OF HOMOSERINE LACTONE, AND PREPARATION METHOD AND USE THEREOF

(71) Applicant: Institute of Pharmacology and Toxicology Academy of Military Medical Sciences P.L.A. CHINA, Beijing (CN)

(72) Inventors: Song Li, Beijing (CN); Junhai Xiao, Beijing (CN); Mingming Zhao, Beijing (CN); Wu Zhong, Beijing (CN); Lili Wang, Beijing (CN); Zhibing Zheng, Beijing (CN); Yunde Xie, Beijing (CN); Xingzhou Li, Beijing (CN); Guoming Zhao, Beijing (CN); Xinbo Zhou, Beijing (CN); Xiaokui Wang, Beijing (CN); Wei Chen, Beijing (CN)

(73) Assignee: INSTITUTE OF PHARMACOLOGY AND TOXICOLOGY ACADEMY OF MILITARY MEDICAL SCIENCES P.L.A. CHINA, Beijing (CN)

( * ) Notice: Subject to any disclaimer, the term of this patent is extended or adjusted under 35 U.S.C. 154(b) by 0 days.

(21) Appl. No.: 14/766,680

(22) PCT Filed: Dec. 10, 2013

(86) PCT No.: PCT/CN2013/088932
§ 371 (c)(1),
(2) Date: Aug. 7, 2015

(87) PCT Pub. No.: WO2014/121633
PCT Pub. Date: Aug. 14, 2014

(65) Prior Publication Data
US 2015/0368217 A1 Dec. 24, 2015

(30) Foreign Application Priority Data
Feb. 8, 2013 (CN) .......................... 2013 1 0049962

(51) Int. Cl.
*C07D 307/33* (2006.01)
*A61K 31/365* (2006.01)
*A61K 45/06* (2006.01)

(52) U.S. Cl.
CPC .......... *C07D 307/33* (2013.01); *A61K 31/365* (2013.01); *A61K 45/06* (2013.01)

(58) Field of Classification Search
None
See application file for complete search history.

(56) References Cited

U.S. PATENT DOCUMENTS

2011/0212860 A1   9/2011   Blackwell et al.

FOREIGN PATENT DOCUMENTS

KR   20080046434 A   5/2008
WO   2008116029 A1   9/2008

OTHER PUBLICATIONS

"Syphilis-prevention", http://www.webmd.com/sexual-conditions/tc/syphilis-prevention?print=true, accessed Apr. 9, 2010.*
"Understanding diarrhea", http://www.webmd.com/digestive-disorders/understanding-diarrhea-prevention, accessed Aug. 25, 2016.*
Rolston. Clinical Infectious Diseases, 2005, 40, S246-52.*
Sifri. Clinical Infectious Diseases, 2008, 47, 1070-6.*
Zhao. Molecules, 2013, 18, 3266-78.*
Wermuth. The Practice of Medicinal Chemistry, 1996, pp. 203-237.*
Silverman. The Organic Chemistry of Drug Design and Drug Action, 2004, title, 25-34.*
Mar. 6, 2014—(WO) International Search Report—App PCT/CN2013/088932.
Yu, Yingying: 'Design, Synthesis and Biological Evaluation of Antagonists of Bacterial Quorum Sensing' Master's Thesis of Jilin University Jul. 15, 2013.
Kim, C. et al.: 'Development of inhibitors against TraR quorum-sensing system in Agrobacterium tumefaciens by molecular modeling of the ligand-receptor interaction' Molecules and Cells vol. 28, No. 5, 2009, pp. 447-453.
Castang, S. et al.: 'N-Sulfonyl homoserine lactones as antagonists of bacterial quorum sensing' Bioorganic & Medicinal Chemistry Letters vol. 14, No. 20, 2004, pp. 5145-5149.

* cited by examiner

*Primary Examiner* — Noble Jarrell
(74) *Attorney, Agent, or Firm* — Banner & Witcoff, Ltd.

(57) ABSTRACT

A derivative of homoserine lactone represented by formula I, and a preparation method and use thereof. The compound has a bacterial quorum-sensing regulatory effect, and can be used for prevention and/or treatment of a disease caused by a bacterial infection.

I

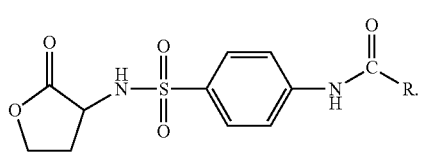

14 Claims, No Drawings

DERIVATIVE OF HOMOSERINE LACTONE, AND PREPARATION METHOD AND USE THEREOF

CROSS-REFERENCE TO RELATED APPLICATIONS

The present application is a U.S. National Phase Entry of International Application No. PCT/CN2013/088932 filed on Dec. 10, 2013, designating the United States of America and claiming priority to Chinese Patent Application No. 201310049962.1, filed Feb. 8, 2013. The present application claims priority to and the benefit of the above-identified applications and the above-identified applications are incorporated by reference herein in their entirety.

TECHNICAL FIELD

The present invention belongs to a medical and chemical engineering field, specifically relates to design and synthesis as well as medical use of a new quorum-sensing regulator.

BACKGROUND

Bacteria communicate with each other by small auto-generated signal molecules, which are termed as auto inducers (AIs in brief). During the growth of bacterial quorum, these auto inducers are produced continuously and are subsequently secreted in the extracellular environment. When the concentration of the signal molecules reaches a threshold value, the expression of relevant genes in bacteria is initiated to adapt to the environmental changes. Such a regulatory system is termed as bacterial quorum sensing (QS) signal systems. QS enables unicellular bacteria to imitate multicellular organisms to accomplish some behaviors that cannot be accomplished when they are unicellular individuals.

In 1970, Nealson et al. discovered QS in *V. fischeri* for the first time, i.e. when bacteria reached a high population concentration, the bacteria generated bioluminescence. In deep study on *V. fischeri*, N-acyl homoserine lactones (AHL) synthesized from LuxI protein activate lux operon of *V. fischeri* by interaction with transcription activating factor luxR. Similar regulatory systems were found in many Gram-positive or Gram-negative bacteria. Their mechanism lies in that when bacteria are at a low population density, the auto inducers synthase gene is expressed at a basic level, resulting in a small amount of autoinduction signal molecules, which are diffused extracellularly and are diluted immediately in the surrounding environment. When the population density of bacteria increases gradually and reaches a threshold value, the autoinduction signal molecules will be permeated into cells and bind to transcriptional regulatory proteins to form a transcriptional regulatory protein-signal molecule polymer, which can bind to a specific DNA sequence of the signal molecule in chromosome to enable the expression of target genes including the synthetic gene of the signal molecule, also resulting in the production of more signal molecules. Such communication and transduction of information among bacteria has been proposed for a long time. However, systematic research is only conducted in the recent 10 years. Such a phenomenon has been demonstrated to be present in many bacteria. For example, *chromobacterium violaceum* has the same mechanism as *V. fischeri*, and can produce C6-HSL as an auto induction molecule, the receptor protein of which is CviR.

Bacterial quorum sensing enables the regulation of expression of some relevant genes in a population of bacteria, such as regulation of generation of antibiotics, bioluminescence, regulation of nitrogen-fixing gene, conjugal transfer of Ti plasmid, expression of virulent gene, pigment generation, bacterial swarming, formation of biofilms, and the like. In the late 1970s, scientists found that naturally occurring or artificially synthesized bacterial quorum-sensing regulators (including agonists or inhibitors) can interfere with the transduction of signaling system and regulate the expression of adverse gene in bacteria.

Bacterial quorum-sensing regulators do not interfere with normal physiological functions of cells in vivo, and thus are regarded as new direction for the development of antibacterials. Bacterial quorum-sensing inhibitors can be used in combination with antibiotics to enhance sensitivity of pathogenic bacteria to antibiotics, and can be used to treat a disease (including, but not limited to peritonitis, cholecystitis, cystitis, diarrhea, endocarditis, gastroenteritis, pyothorax, sepsis and other various diseases) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, to treat a disease caused by drug-resistant Gram-negative bacteria not sensitive to current antibiotics.

The purpose of the invention is to synthesize new bacterial quorum-sensing regulator, for use in the treatment of a disease caused by a Gram-negative bacterium, particularly a disease caused by drug-resistant Gram-negative bacteria.

BRIEF SUMMARY

In the first aspect, the present invention provides a derivative of homoserine lactone represented by formula I, a racemate or optical isomer, a pharmaceutically acceptable salt, a solvate or a hydrate thereof,

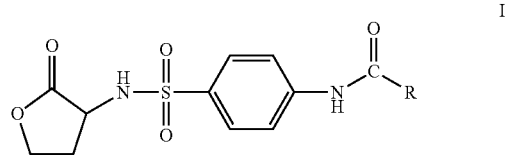

Wherein R is C1-12 linear or branched alkyl, or phenyl, said alkyl or phenyl is optionally mono-substituted or multi-substituted by a substituent selected from the group consisting of: phenyl, substituted or unsubstituted C1-5 linear or branched alkyl, halogen, cyano, trifluoromethyl, hydroxyl, nitro, substituted or unsubstituted C1-5 alkoxyl.

In one embodiment according to the present invention, in the derivative of homoserine lactone represented by formula I, a racemate or optical isomer, a pharmaceutically acceptable salt, a solvate or a hydrate thereof according to the first aspect of the present invention, R is C1-9 linear or branched alkyl, or phenyl, said alkyl or phenyl is optionally mono-substituted or multi-substituted by a substituent selected from the group consisting of: phenyl, C1-5 linear or branched alkyl, C1-5 linear or branched alkyl mono-substituted or multi-substituted by halogen, halogen, cyano, trifluoromethyl, hydroxyl, nitro, C1-5 alkoxyl, C1-5 alkoxyl mono-substituted or multi-substituted by halogen.

In one embodiment according to the present invention, in the derivative of homoserine lactone represented by formula I, a racemate or optical isomer, a pharmaceutically acceptable salt, a solvate or a hydrate thereof according to the first aspect of the present invention, R is C1-9 linear or branched alkyl, or phenyl, said alkyl or phenyl is optionally mono-substituted or multi-substituted by a substituent selected from the group consisting of: phenyl, C1-4 linear or branched alkyl, C1-4 linear or branched alkyl mono-substituted or multisubstituted by halogen, halogen, cyano, trifluoromethyl, hydroxyl, nitro, C1-4 alkoxyl, C1-4 alkoxyl mono-substituted or multi-substituted by halogen.

In one embodiment according to the present invention, in the derivative of homoserine lactone represented by formula I, a racemate or optical isomer, a pharmaceutically acceptable salt, a solvate or a hydrate thereof according to the first aspect of the present invention, R is methyl, ethyl, n-propyl, isopropyl, n-butyl, sec-butyl, tert-butyl, pentyl, hexyl, heptyl, octyl, nonyl, phenyl, chlorophenyl, bromophenyl, fluorophenyl, nitrophenyl, cyanophenyl, methylphenyl, ethylphenyl, benzyl, trifluoromethylphenyl, methoxyphenyl, ethoxyphenyl, or halogenated methylphenyl.

In one embodiment according to the present invention, the derivative of homoserine lactone represented by formula I, a racemate or optical isomer, a pharmaceutically acceptable salt, a solvate or a hydrate thereof according to the first aspect of the present invention, is selected from the group consisting of:
(S)-N-(4-(N-(2-oxotetrahydrofuran-3-yl)sulfamoyl)phenyl) propanamide (Compound 1),
(S)-N-(4-(N-(2-oxotetrahydrofuran-3-yl)sulfamoyl)phenyl) butyrylamide (Compound 2),
(S)-N-(4-(N-(2-oxotetrahydrofuran-3-yl)sulfamoyl)phenyl) pentanamide (Compound 3),
(S)-N-(4-(N-(2-oxotetrahydrofuran-3-yl)sulfamoyl)phenyl) hexanamide (Compound 4),
(S)-N-(4-(N-(2-oxotetrahydrofuran-3-yl)sulfamoyl)phenyl) heptanamide (Compound 5),
(S)-N-(4-(N-(2-oxotetrahydrofuran-3-yl)sulfamoyl)phenyl) octanamide (Compound 6),
(S)-N-(4-(N-(2-oxotetrahydrofuran-3-yl)sulfamoyl)phenyl) pelargonamide (Compound 7),
(S)-N-(4-(N-(2-oxotetrahydrofuran-3-yl)sulfamoyl)phenyl) decanamide (Compound 8),
(S)-N-(4-(N-(2-oxotetrahydrofuran-3-yl)sulfamoyl)phenyl) benzamide (Compound 9),
(S)-4-methyl-N-(4-(N-(2-oxotetrahydrofuran-3-yl)sulfamoyl)phenyl)benzamide (Compound 10),
(S)-4-ethyl-N-(4-(N-(2-oxotetrahydrofuran-3-yl)sulfamoyl)phenyl)benzamide (Compound 11),
(S)-4-bromo-N-(4-(N-(2-oxotetrahydrofuran-3-yl)sulfamoyl)phenyl)benzamide (Compound 12),
(S)-4-propyl-N-(4-(N-(2-oxotetrahydrofuran-3-yl)sulfamoyl)phenyl)benzamide (Compound 13),
(S)-4-chloro-N-(4-(N-(2-oxotetrahydrofuran-3-yl)sulfamoyl)phenyl)benzamide (Compound 14),
(S)-4-(chloromethyl)-N-(4-(N-(2-oxotetrahydrofuran-3-yl) sulfamoyl)phenyl) benzamide (Compound 15),
(S)-4-(tert-butyl)-N-(4-(N-(2-oxotetrahydrofuran-3-yl)sulfamoyl)phenyl)benzamide (Compound 16),
(S)-4-fluoro-N-(4-(N-(2-oxotetrahydrofuran-3-yl)sulfamoyl)phenyl)benzamide (Compound 17),
(S)-4-cyano-N-(4-(N-(2-oxotetrahydrofuran-3-yl)sulfamoyl)phenyl)benzamide (Compound 18),
(S)-N-(4-(N-(2-oxotetrahydrofuran-3-yl)sulfamoyl)phenyl) phenylacetamide (Compound 19),
(S)-3-methyl-N-(4-(N-(2-oxotetrahydrofuran-3-yl)sulfamoyl)phenyl)benzamide (Compound 20),
(S)-4-methoxyl-N-(4-(N-(2-oxotetrahydrofuran-3-yl)sulfamoyl)phenyl)benzamide (Compound 21),
(S)-3-chloro-N-(4-(N-(2-oxotetrahydrofuran-3-yl)sulfamoyl)phenyl)benzamide (Compound 22),
(S)-3-fluoro-N-(4-(N-(2-oxotetrahydrofuran-3-yl)sulfamoyl)phenyl)benzamide (Compound 23),
(S)-2-fluoro-N-(4-(N-(2-oxotetrahydrofuran-3-yl)sulfamoyl)phenyl)benzamide (Compound 24),
(S)-2-ethyoxyl-N-(4-(N-(2-oxotetrahydrofuran-3-yl)sulfamoyl)phenyl)benzamide (Compound 25),
(S)-4-nitro-N-(4-(N-(2-oxotetrahydrofuran-3-yl)sulfamoyl) phenyl)benzamide (Compound 26),
(S)-2-trifluoromethyl-N-(4-(N-(2-oxotetrahydrofuran-3-yl) sulfamoyl)phenyl)benzamide (Compound 27),
(S)-2-chloro-N-(4-(N-(2-oxotetrahydrofuran-3-yl)sulfamoyl)phenyl)benzamide (Compound 28), and
(D)-2-fluoro-N-(4-(N-(2-oxotetrahydrofuran-3-yl)sulfamoyl)phenyl)benzamide (Compound 29).

In one embodiment according to the present invention, the derivative of homoserine lactone represented by formula I, a racemate or optical isomer, a pharmaceutically acceptable salt, a solvate or a hydrate thereof according to the first aspect of the present invention, is selected from the following group consisting of:
(S)-N-(4-(N-(2-oxotetrahydrofuran-3-yl)sulfamoyl)phenyl) propanamide (Compound 1),
(S)-N-(4-(N-(2-oxotetrahydrofuran-3-yl)sulfamoyl)phenyl) butyrylamide (Compound 2),
(S)-N-(4-(N-(2-oxotetrahydrofuran-3-yl)sulfamoyl)phenyl) pentanamide (Compound 3),
(S)-N-(4-(N-(2-oxotetrahydrofuran-3-yl)sulfamoyl)phenyl) hexanamide (Compound 4),
(S)-N-(4-(N-(2-oxotetrahydrofuran-3-yl)sulfamoyl)phenyl) heptanamide (Compounds),
(S)-N-(4-(N-(2-oxotetrahydrofuran-3-yl)sulfamoyl)phenyl) octanamide (Compound 6),
(S)-N-(4-(N-(2-oxotetrahydrofuran-3-yl)sulfamoyl)phenyl) benzamide (Compound 9),
(S)-4-bromo-N-(4-(N-(2-oxotetrahydrofuran-3-yl)sulfamoyl)phenyl)benzamide (Compound 12),
(S)-4-chloro-N-(4-(N-(2-oxotetrahydrofuran-3-yl)sulfamoyl)phenyl)benzamide (Compound 14),
(S)-4-(tert-butyl)-N-(4-(N-(2-oxotetrahydrofuran-3-yl)sulfamoyl)phenyl)benzamide (Compound 16),
(S)-4-fluoro-N-(4-(N-(2-oxotetrahydrofuran-3-yl)sulfamoyl)phenyl)benzamide (Compound 17),
(S)-3-methyl-N-(4-(N-(2-oxotetrahydrofuran-3-yl)sulfamoyl)phenyl)benzamide (Compound 20),
(S)-3-chloro-N-(4-(N-(2-oxotetrahydrofuran-3-yl)sulfamoyl)phenyl)benzamide (Compound 22),
(S)-3-fluoro-N-(4-(N-(2-oxotetrahydrofuran-3-yl)sulfamoyl)phenyl)benzamide (Compound 23),
(S)-2-fluoro-N-(4-(N-(2-oxotetrahydrofuran-3-yl)sulfamoyl)phenyl)benzamide (Compound 24),
(S)-2-trifluoromethyl-N-(4-(N-(2-oxotetrahydrofuran-3-yl) sulfamoyl)phenyl)benzamide (Compound 27), and
(S)-2-chloro-N-(4-(N-(2-oxotetrahydrofuran-3-yl)sulfamoyl)phenyl)benzamide (Compound 28).

In one embodiment according to the present invention, the derivative of homoserine lactone represented by formula I, a racemate or optical isomer, a pharmaceutically acceptable salt, a solvate or a hydrate thereof according to the first aspect of the present invention, is selected from the following group consisting of:
(S)-4-bromo-N-(4-(N-(2-oxotetrahydrofuran-3-yl)sulfamoyl)phenyl)benzamide (Compound 12),
(S)-4-(chloromethyl)-N-(4-(N-(2-oxotetrahydrofuran-3-yl)sulfamoyl)phenyl)benzamide (Compound 15), In the second aspect, the present invention provides a method for preparing the derivative of homoserine lactone represented by formula I according to the first aspect of the present invention, comprising the following steps of: reacting an intermediate represented by formula 3 with acyl chloride represented by RCOCl, to prepare the derivative of homoserine lactone represented by formula I,

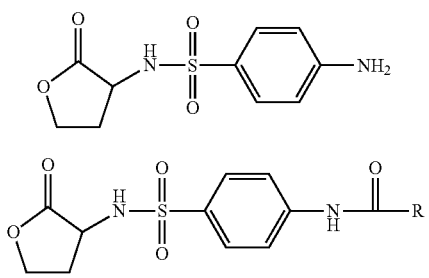

wherein R is defined as the first aspect of the present invention.

In one embodiment according to the present invention, in the method according to the second aspect of the present invention, the intermediate represented by formula 3 is obtained by reacting acetamino-benzenesulfonyl chloride with homoserine lactone hydrobromide.

In one embodiment according to the present invention, in the method according to the second aspect of the present invention, the reaction scheme is shown as follow:

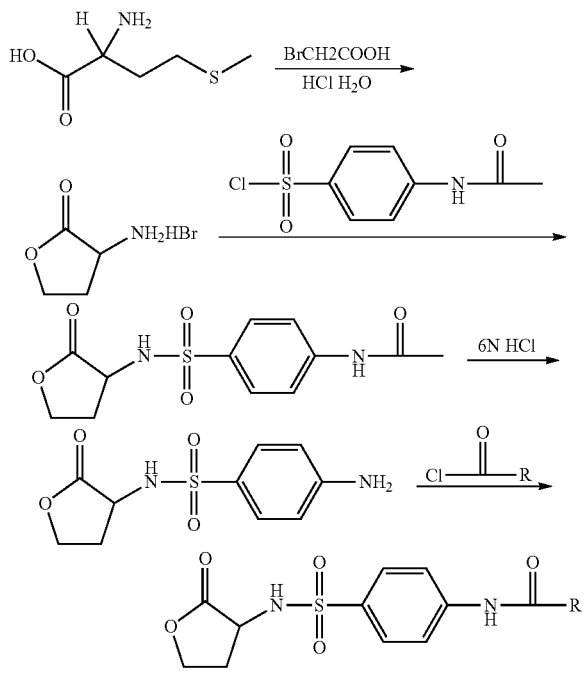

wherein R is defined as the first aspect of the present invention.

In the third aspect, the present invention provides a pharmaceutical composition, comprising the derivative of homoserine lactone represented by formula I, a racemate or optical isomer, a pharmaceutically acceptable salt, a solvate or a hydrate thereof according to the first aspect of the present invention, and optionally one or more pharmaceutically acceptable carriers or excipients.

The derivative of homoserine lactone represented by formula I, a racemate or optical isomer, a pharmaceutically acceptable salt, a solvate or a hydrate thereof according to the first aspect of the present invention, as a bacterial quorum sensing regulator, may be used in combination with antibiotics to enhance sensitivity of pathogenic bacteria to antibiotics. Thus, in one specific embodiment of the present invention, the pharmaceutical composition according to the third aspect of the invention may further comprise one or more antibiotics.

In the forth aspect, the present invention provides use of the derivative of homoserine lactone represented by formula I, a racemate or optical isomer a pharmaceutically acceptable salt, a solvate or a hydrate thereof according to the first aspect of the present invention, in the preparation of a medicament as a bacterial quorum sensing regulator.

In the fifth aspect, the present invention provides use of the pharmaceutical composition according to the third aspect of the present invention in the preparation of a medicament as a bacterial quorum sensing regulator.

In one specific embodiment of the present invention, in the use according to the fourth or fifth aspect of the present invention, said bacterial quorum sensing regulator may be a bacterial quorum sensing agonist, or a bacterial quorum sensing inhibitor.

Specifically, in one embodiments of the present invention, the derivative of homoserine lactone represented by formula I selected from the following compounds, a racemate or optical isomer, a pharmaceutically acceptable salt, a solvate or a hydrate thereof, may be used in the preparation a medicament as a bacterial quorum sensing agonist,
(S)-4-bromo-N-(4-(N-(2-oxotetrahydrofuran-3-yl)sulfamoyl)phenyl)benzamide (Compound 12), and
(S)-4-(chloromethyl)-N-(4-(N-(2-oxotetrahydrofuran-3-yl) sulfamoyl)phenyl)benzamide (Compound 15).

Specifically, in one embodiments of the present invention, the derivative of homoserine lactone represented by formula I selected from the following compounds, a racemate or optical isomer, a pharmaceutically acceptable salt, a solvate or a hydrate thereof, may be used in preparation a medicament as a bacterial quorum sensing inhibitor,
(S)-N-(4-(N-(2-oxotetrahydrofuran-3-yl)sulfamoyl)phenyl) propanamide (Compound 1),
(S)-N-(4-(N-(2-oxotetrahydrofuran-3-yl)sulfamoyl)phenyl) butyrylamide (Compound 2),
(S)-N-(4-(N-(2-oxotetrahydrofuran-3-yl)sulfamoyl)phenyl) pentanamide (Compound 3),
(S)-N-(4-(N-(2-oxotetrahydrofuran-3-yl)sulfamoyl)phenyl) hexanamide (Compound 4),
(S)-N-(4-(N-(2-oxotetrahydrofuran-3-yl)sulfamoyl)phenyl) heptanamide (Compound 5),
(S)-N-(4-(N-(2-oxotetrahydrofuran-3-yl)sulfamoyl)phenyl) octanamide (Compound 6),
(S)-N-(4-(N-(2-oxotetrahydrofuran-3-yl)sulfamoyl)phenyl) benzamide (Compound 9),
(S)-4-bromo-N-(4-(N-(2-oxotetrahydrofuran-3-yl)sulfamoyl)phenyl)benzamide (Compound 12), (S)-4-chloro-N-(4-(N-(2-oxotetrahydrofuran-3-yl)sulfamoyl)phenyl)benzamide (Compound 14),
(S)-4-(tert-butyl)-N-(4-(N-(2-oxotetrahydrofuran-3-yl)sulfamoyl)phenyl)benzamide (Compound 16),
(S)-4-fluoro-N-(4-(N-(2-oxotetrahydrofuran-3-yl)sulfamoyl)phenyl)benzamide (Compound 17),
(S)-3-methyl-N-(4-(N-(2-oxotetrahydrofuran-3-yl)sulfamoyl)phenyl)benzamide (Compound 20),
(S)-3-chloro-N-(4-(N-(2-oxotetrahydrofuran-3-yl)sulfamoyl)phenyl)benzamide (Compound 22),
(S)-3-fluoro-N-(4-(N-(2-oxotetrahydrofuran-3-yl)sulfamoyl)phenyl)benzamide (Compound 23),
(S)-2-fluoro-N-(4-(N-(2-oxotetrahydrofuran-3-yl)sulfamoyl)phenyl)benzamide (Compound 24),
(S)-2-trifluoromethyl-N-(4-(N-(2-oxotetrahydrofuran-3-yl)sulfamoyl)phenyl)benzamide (Compound 27), and
(S)-2-chloro-N-(4-(N-(2-oxotetrahydrofuran-3-yl)sulfamoyl)phenyl)benzamide (Compound 28).

The derivative of homoserine lactone represented by formula I, a racemate or optical isomer, a pharmaceutically acceptable salt, a solvate or a hydrate thereof according to the first aspect of the present invention, as a bacterial quorum sensing regulator, can inhibit or agonize bacterial quorum sensing, does not interfere with normal physiological functions of cells in vivo, and thus is regarded as the new direction for the development of antibacterials. In particular, the derivative as quorum sensing inhibitor can be used in combination with antibiotics, to enhance sensitivity of pathogenic bacterium to antibiotics, and can be used to treat a disease or infection (including, but not limited to peritonitis, cholecystitis, cystitis, diarrhea, endocarditis, gastroenteritis, pyothorax, sepsis and other various diseases) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, to treat a disease caused by drug-resistant Gram-negative bacteria which are not sensitive to current antibiotics.

Therefore, in the sixth aspect, the present invention provides use of the derivative of homoserine lactone represented by formula I, a racemate or optical isomer, a pharmaceutically acceptable salt, a solvate or a hydrate thereof according to the aspect of the present invention, in the preparation of a medicament for prevention and/or treatment of a decease caused by a bacterial infection.

In seventh aspect, the present invention provides use of the pharmaceutical composition according to the third aspect of the present invention in the preparation of a medicament for prevention and/or treatment of a decease caused by bacterial quorum sensing.

In the use according to the sixth or the seventh aspect of the present invention, said disease caused by bacterial quorum sensing includes, but is not limited to an infection or a disease (including, but not limited to peritonitis, cholecystitis, cystitis, diarrhea, endocarditis, gastroenteritis, pyothorax, sepsis and other various diseases) caused by a Gram-negative bacterium such as *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, the diseases caused by drug-resistant Gram-negative bacteria not sensitive to current antibiotics.

In the eighth aspect, the present invention provides use of the derivative of homoserine lactone represented by formula I, a racemate or optical isomer, a pharmaceutically acceptable salt, a solvate or a hydrate thereof according to the first aspect of the present invention as a tool drug for studying bacterial quorum sensing regulation.

DETAILED DESCRIPTION

The terms and phrases used in the present invention have the general meanings well known by a person skilled in the art, however, if they are specifically defined herein, the meanings defined herein shall prevail.

As used herein, the term "alkyl" has the general meanings well known in the art, and generally includes linear or branched alkyl. For example, the "alkyl" described in the invention may be C1-C12 alkyl, C1-C10 alkyl, C1-C6 alkyl or C1-C4 alkyl. The C1-C12 alkyl, C1-C10 alkyl, C1-C6 alkyl or C1-C4 alkyl refers to alkyl containing 1 to 12, 1 to 10, 1 to 6, or 1 to 4 (including end values) carbon atoms, respectively. The "alkyl" described in the invention includes, but is not limited to methyl, ethyl, propyl, isopropyl, n-butyl, sec-butyl, tert-butyl, pentyl, hexyl, etc.

As used herein, the term "halogen" has the general meanings well known in the art, and generally includes F, Cl, Br, I, as well as their isotopes, and are preferably F, Cl and Br in the invention.

As used herein, the groups represented by the following terms have the general meanings well known in the art: nitrile group, trifluoromethyl, trifluoromethoxyl, hydroxyl, nitro, alkoxyl, and cyano.

As used herein, the terms "racemate" or "optical isomer" have the general meanings well known in the art.

According to the present invention, the above compounds of Formula I can be prepared by the following typical and exemplified method, comprising the steps of:

1) adding methionine into the mixed solution composed of water, 2-isopropanol and glacial acetic acid, and stirring well, and then adding bromoacetic acid, heating and refluxing for 2 hours, then cooling to room temperature and being concentrated into yellow oily liquid, then adding the mixture of 2-isopropanol and toluene (1:1 v/v), concentrating after mixed well, to get orange oily liquid. Adding dioxane and concentrated hydrochloric acid into the oily liquid, heating at 50° C. for 10 mins, stirring overnight after heating, putting the reaction system in ice bath, precipitating yellow solid, filtrating under vacuum, washing the filter cake to white with 2-isopropanol, to get intermediate 1;

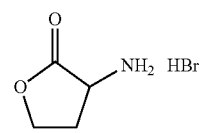

1

2) adding p-acetamino-benzenesulfonyl chloride into the ethanol solution of intermediate 1 at 0° C. in batches, stirring at room temperature overnight, pouring the reactant into ice water and stirring strongly for one hour, filtrating and collecting the precipitated white solid, washing with ice water, drying in vacuum, and recrystallizing in ethanol, to get white solid (Intermediate 2);

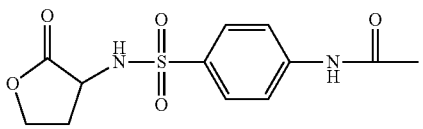

3) adding 6N hydrochloric acid into the ethanol solution of the intermediate 2, heating and refluxing for 3 hours, drying the reaction mixture by distillation under reduced pressure, dissolving the residue in water and adjusting to pH 7-8 with an aqueous ammonia, stirring for 1 hour, filtrating and collecting the precipitated white solid, washing with ice water, drying in vacuum, and recrystallizing in ethanol, to get white solid (Intermediate 3);

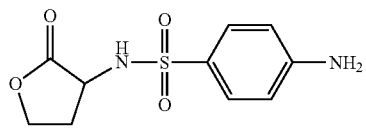

4) putting intermediate 3 in a three-necked flask, adding triethylamine, slowly adding dropwise acyl chloride (RCOCl) at 0° C. in ice bath, finishing adding within 15 minutes, removing the ice bath, stirring at room temperature overnight, drying the reaction solution by distillation under reduced pressure, performing column chromatography (eluent: methanol/dichloromethane), to get white solid product (compound of formula I)

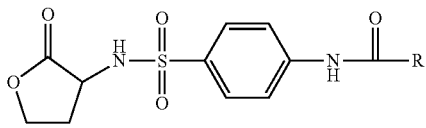

wherein R is defined as the first aspect of the present invention.

Beneficial Effects of the Invention

The invention synthesizes a class of new bacterial quorum-sensing regulators represented by Formula I, which do not interfere with normal physiological functions of cells in vivo, and thus are regarded as new direction for the development of antibacterials, wherein the bacterial quorum-sensing inhibitors can be used in combination with antibiotics, to treat an infection or a disease (including, but not limited to peritonitis, cholecystitis, cystitis, diarrhea, endocarditis, gastroenteritis, pyothorax, sepsis and other various diseases) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae,* and *Vibrio Parahemolyticus,* particularly, to treat a disease caused by drug-resistant Gram-negative bacteria not sensitive to current antibiotics.

The invention is further described by the following intermediates and examples. However, it should be understood that these intermediates and examples are only used to describe the invention more detailedly, and should not be understood as restricting the invention in any manner.

The invention describes the materials and experimental methods used in the experiments generally and/or in detail. Although many materials and methods used to achieve the purpose of the invention are well known in the art, the invention still describes them as detailedly as possible. A person skilled in the art knows that unless otherwise specified, the materials and methods used in the invention are well known in the art.

In the following examples, the melting points of the compounds were measured by YRT-3 type melting point apparatus, wherein the temperature was not calibrated. The specific rotatory power was measured by Polaar 3005 type Accuracy Automatic Polarimeter from OA Company. $^1$H-NMR spectra were measured by Bruker ARX 400 type NMR spectrometer. FAB mass spectra were measured by Zabspect High Resolution mass spectrometer.

Preparation of Intermediates

Preparation of Intermediate 1

(L)-homoserine lactone hydrobromide

Intermediate 1

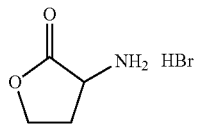

15.0 g (100 mmol) L-methionine was added into the mixed solution composed of 60 ml water, 60 ml 2-isopropanol and 24 ml glacial acetic acid and was well stirred, and then 14.0 g (100 mmol) bromoacetic acid was added, and the mixture heated under reflux for 2 hours, and cooled to room temperature and concentrated into a yellow oily liquid. Then 10 ml mixture of 2-isopropanol and toluene (1:1 v/v) was added into the yellow oily liquid, the mixture was concentrated to get an orange oily liquid. 40 ml dioxane and 20 ml concentrated hydrochloric acid were added into the oily liquid, and heated at 50° C. for 10 mins, and were stirred overnight after heated, the reaction system was then placed in ice bath for 4 hours, light yellow solid was precipitated, filtrated under vacuum, washed the filter cake to white with 2-isopropanol, to get 9.51 g product (intermediate 1), with a yield of 52%.

$^1$H-NMR(400MHz,D$_2$O)δppm:4.40(1H,t,J=12.0Hz, J=12.0Hz),4.27(1H,m),2.60(1H, m),2.26(1H,m);EI-MS(m/z):102.1[M+H]$^+$;m.p.220-224° C.; $[α]_D^{25}$=−23.4(c=0.1, H$_2$O).

Preparation of Intermediate 2

(S)-N-(4-(N-(2-oxotetrahydrofuran-3-yl)sulfamoyl) phenyl)acetamide

Intermediate2

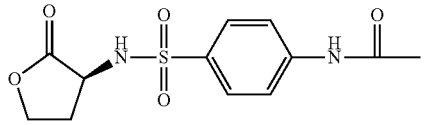

12.3 g (52 mmol) p-acetamino-benzenesulfonyl chloride was added into 80 ml ethanol solution containing 8.0 g (43 mmol) (L)-homoserine lactone hydrobromide (intermediate 1) and 8.7 g (86 mmol) triethylamine at 0° C. in batches, and stirred at room temperature overnight, the reactant was poured into ice water (200 mL), stirred strongly for 1 hours, the precipitated white solid was collected by filtration, washed with ice water and dried in vacuum, recrystallized in ethanol, to get 7.47 g white solid (Intermediate 2), with a yield of 57%.

$^1$H-NMR(400MHz,DMSO)δppm:10.33(1H,s),8.16(1H,d,J=8.0Hz),7.75(4H,m),4.34(1H,m),4.21(1H,m),4.08(1H,m),2.08(4H,m),1.79(1H, m); EI-MS (m/z): 299.34 [M+H]$^+$; m.p. 174-176° C.

Preparation of Intermediate 3

(S)-4-amino-N-(2-oxotetrahydrofuran-3-yl)benzene sulfonamide

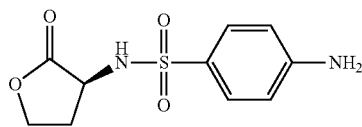

Intermediate 3

12 ml 6N hydrochloric acid was added into 25 ml ethanol solution of 6.0 g (20.1 mmol) (S)-N-(4-(N-(2-oxotetrahydrofuran-3-yl)sulfamoyl)phenyl) acetamide, and was heated and refluxed for 3 hours, the reaction mixture was dried by distillation under reduced pressure, the residue was dissolved in water and adjusted to pH 7-8 with 1N aqueous ammonia, stirred for 1 hour. The precipitated white solid was collected by filtration and washed with ice-water, dried in vacuum, recrystallized in ethanol, to get 3.4 g white solid (Intermediate 3), with a yield of 63%.

$^1$H-NMR (400MHz,DMSO)δppm:7.72(1H,d,J=9.2Hz),7.45(2H,d,J=8.4Hz),6.61(2H,d,J=8.8Hz),5.95(2H,m),4.22(2H,m),4.08(1H,m),2.05(1H,m),1.78(1H,m);EI-MS (m/z): 256.4[M+H]$^+$;m.p. 163-165° C.

EXAMPLES

Example 1

(S)-N-(4-(N-(2-oxotetrahydrofuran-3-yl)sulfamoyl) phenyl) propanamide (Compound 1)

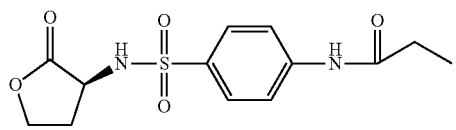

Compound 1

0.5 g (1.9 mmol) (S)-4-amino-N-(2-oxotetrahydrofuran-3-yl)benzene sulfonamide (intermediate 3) was put a three-necked flask containing 10 ml anhydrous dichloromethane, 0.38 g (3.8 mmol) triethylamine was added, 0.21 ml (2.3 mmol) propionyl chloride was added dropwise at 0° C. in ice bath, the addition was finished within 15 minutes, the ice bath was removed, the mixture was stirred at room temperature overnight, the reaction solution was dried by distillation under reduced pressure, column chromatography was performed (eluent: methanol/dichloromethane (at a ratio of 1:20 by volume)), to get 0.33 g white solid product (Compound 1), with a yield of 55%.

$^1$H-NMR(400MHz,DMSO)δppm:10.27(1H,s),8.16(1H,d,J=9.2Hz),7.79(4H,m),4.34(1H,m),4.21(1H,m),4.08(1H,m),2.37(2H,m),2.10(1H,m),1.81(1H,m),1.08(3H,t,J=8.0Hz,J=7.6Hz);EI-MS(m/z):312.3[M+H]$^+$;m.p.179-181° C.; $[α]_D^{25}$=+15.2(c=0.1,H$_2$O).

Example 2

(S)-N-(4-(N-(2-oxotetrahydrofuran-3-yl)sulfamoyl) phenyl)butyrylamide (Compound 2)

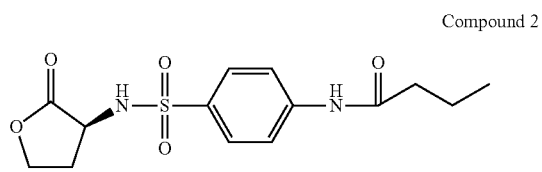 [SMILES: CCCC(=O)Nc1ccc(S(=O)(=O)N[C@H]2CCOC2=O)cc1]

Compound 2

Intermediate 3 and butyryl chloride were used as raw materials, and operations were performed as they were in Example 1, to get white solid product (compound 2).

$^1$H-NMR(400MHz,DMSO)δppm:10.28(1H,s),8.17(1H,d,J=8.0Hz),7.77(4H,m)4.34(1H,m),4.21(1H,m),4.08(1H,m),2.32(2H,m),2.10(1H,m),1.80(1H,m),1.64(2H,m),0.91(3H,t,J=7.3Hz,J=7.6Hz);EI-MS(m/z): 327.4[M+H]$^+$; m.p.180-182° C.

Example 3

(S)-N-(4-(N-(2-oxotetrahydrofuran-3-yl)sulfamoyl) phenyl)pentanamide (Compound 3)

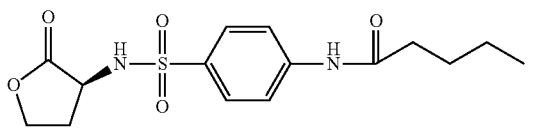

Compound 3

Intermediate 3 and pentanoyl chloride were used as raw materials, and operations were performed as they were in Example 1, to get white solid product (Compound 3).

$^1$H-NMR(400MHz,DMSO)δppm:10.28(1H,s),8.17(1H,d,J=9.6Hz),7.76(4H,m),4.34(1H,m),4.19(1H,m),4.07(1H,m),2.35(2H,m),2.09(1H,m),1.80(1H,m),1.57(1H,m),1.33(1H,m),0.89(3H,t,J=8.0Hz,J=8.0Hz);EI-MS(m/z):341.4[M+H]$^+$; m.p.174-176° C.; $[α]_D^{25}$=+5.7° (c=0.08,CH$_3$OH).

Example 4

(S)-N-(4-(N-(2-oxotetrahydrofuran-3-yl)sulfamoyl)phenyl)hexanamide (Compound 4)

Compound 4

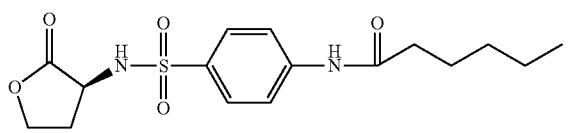

Intermediate 3 and hexanoyl chloride were used as raw materials, and operations were performed as they were in Example 1, to get white solid product (compound 4).

$^1$H-NMR(400MHz,DMSO)δppm:10.24(1H,s),8.13(1H,d,J=9.2Hz),7.76(4H,m),4.30(1H,m),4.17(1H,m),4.05(1H,m),2.30(2H,m),2.09(1H,m),1.76(1H,m),1.56(2H,m),1.26(4H,m),0.83(3H,m);EI-MS(m/z):355.4[M+H]$^+$;m.p.142-143° C.; $[α]_D^{25}$=+6.4° (c=0.10,CH$_3$OH).

Example 5

(S)-N-(4-(N-(2-oxotetrahydrofuran-3-yl)sulfamoyl)phenyl)heptamide (Compound 5)

Compound 5

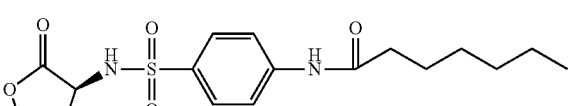

Intermediate 3 and heptanoyl chloride were used as raw materials, and operations were performed as they were in Example 1, to get white solid product (compound 5).

$^1$H-NMR(400MHz,DMSO)δppm:10.26(1H,s),8.16(1H,d,J=9.2Hz),7.76(4H,m),4.34(1H,m),4.21(1H,m),4.07(1H,m),2.34(2H,m),2.09(1H,m),1.80(1H,m), 1.58(2H,m),1.32(6H,m),0.88(3H,m);EI-MS(m/z):369.5[M+H]$^+$;m.p.143-144° C.; $[α]_D^{25}$=+4.7(c=0.10,CH$_3$OH).

Example 6

(S)-N-(4-(N-(2-oxotetrahydrofuran-3-yl)sulfamoyl)phenyl)octanamide (Compound 6)

Compound 6

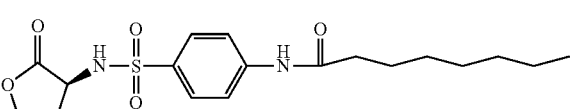

Intermediate 3 and octanoyl chloride were used as raw materials, and operations were performed as they were in Example 1, to get white solid product (compound 6).

$^1$H-NMR(400MHz,DMSO)δppm:10.27(1H,s),8.17(1H,d,J=8.0Hz),7.76(4H,m),4.34(1H,m),4.19(1H,m),4.08(1H,m),2.33(2H,m),2.10(1H,m),1.80(1H,m),1.58(2H,m),1.28(8H,m),0.87(3H,m);EI-MS(m/z):383.5[M+H]$^+$;m.p.146-148° C.; $[α]_D^{25}$=+5.6(c=0.11,CH$_3$OH).

Example 7

(S)-N-(4-(N-(2-oxotetrahydrofuran-3-yl)sulfamoyl)phenyl)pelargonamide (Compound 7)

Compound 7

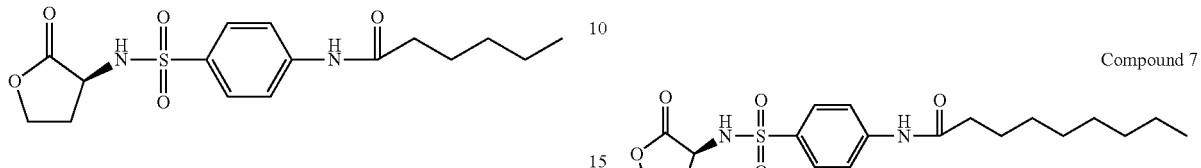

Intermediate 3 and pelargonyl chloride were used as raw materials, and operations were performed as they were in Example 1, to get white solid product (compound 7).

$^1$H-NMR(400MHz,DMSO)δppm:10.27(1H,s),8.16(1H,d,J=9.0 Hz),7.78(4H,m),4.34(1H,m),4.21(1H,m),4.08(1H,m),2.33(2H,m),2.10(1H,m),1.80(1H,m),1.58(2H,m),1.28(10H,m),0.87(3H,m);EI-MS(m/z):397.5[M+H]$^+$;m.p.150-152° C., $[α]_D^{25}$=+4.5(c=0.12,CH$_3$OH).

Example 8

(S)-N-(4-(N-(2-oxotetrahydrofuran-3-yl)sulfamoyl)phenyl)decanamide (Compound 8)

Compound 8

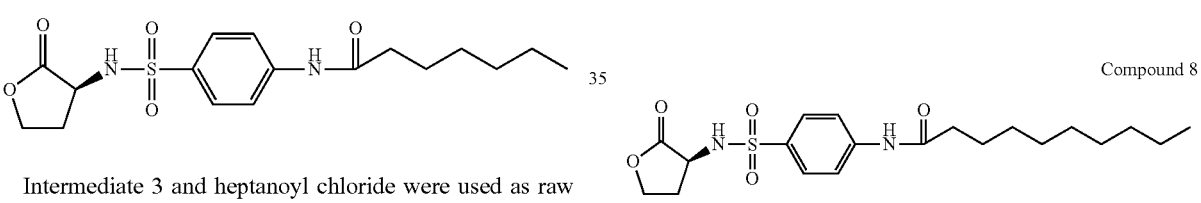

Intermediate 3 and decanoyl chloride were used as raw materials, and operations were performed as they were in Example 1, to get white solid product (compound 8).

$^1$H-NMR(400MHz,DMSO)δppm:10.27(1H,s),8.16 (1H,d,J=9.2Hz),7.75(4H,m),4.34(1H,m),4.21(1H,m),4.07(1H,m),2.33(2H,m),2.10(1H,m),1.80(1H,m),1.58(2H,m),1.27(12H,m),0.87(3H,t,J=6.8Hz,J=7.8Hz);EI-MS(m/z):397.5[M+H]$^+$;m.p.154-156° C., $[α]_D^{25}$=+5.6(c=0.12,CH$_3$OH).

Example 9

(S)-N-(4-(N-(2-oxotetrahydrofuran-3-yl)sulfamoyl)phenyl)benzamide (Compound 9)

Compound 9

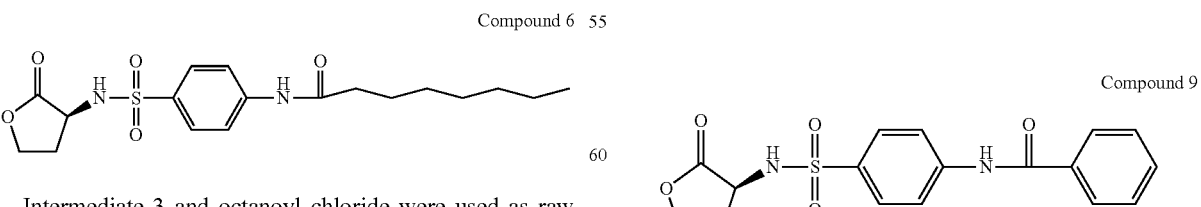

Intermediate 3 and benzoyl chloride were used as raw materials, and the operations were performed as they were in Example 1, to get white solid product (Compound 9).

$^1$H-NMR(400MHz,DMSO)δppm:10.62(1H,s),8.20(1H,d,J=8.0Hz),7.79(4H,m),7.83(2H,d,J=8.8Hz),7.57(3H,m), 4.38 (1H,m),4.23(1H,m), 4.12(1H,m),2.14(1H,m),1.86(1H,m); EI-MS(m/z):361.4[M+H]$^+$;m.p.222-224° C.; $[α]_D^{25}$=+9.1 (c=0.10,CH$_3$OH).

Example 10

(S)-4-methyl-N-(4-(N-(2-oxotetrahydrofuran-3-yl) sulfamoyl)phenyl)benzamide (Compound 10)

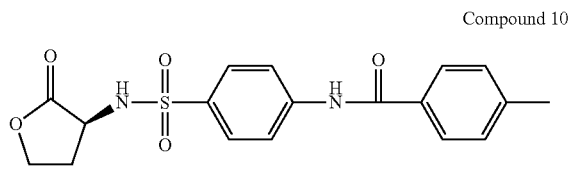 [SMILES: Cc1ccc(C(=O)Nc2ccc(S(=O)(=O)N[C@H]3CCOC3=O)cc2)cc1]

Compound 10

Intermediate 3 and 4-methyl benzoyl chloride were used as raw materials, and operations were performed as they were in Example 1, to get white solid product (Compound 10).

$^1$H-NMR (400MHz,DMSO)δppm:10.52(1H,s),8.20(1H, d,J=8.0Hz),7.98(2H,d,J=7.6Hz),7.90(4H,d,J=8.0Hz),7.37 (2H,d,J=8.0Hz),4.37(1H,m),4.23(1H,m),4.11(1H,m),2.39 (3H,s),2.15(1H,m),1.83(1H,m);EI-MS(m/z):375.2[M+H]$^+$.

Example 11

(S)-4-ethyl-N-(4-(N-(2-oxotetrahydrofuran-3-yl) sulfamoyl)phenyl)benzamide (Compound 11)

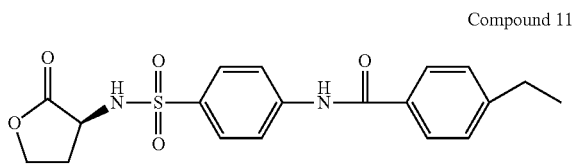 [SMILES: CCc1ccc(C(=O)Nc2ccc(S(=O)(=O)N[C@H]3CCOC3=O)cc2)cc1]

Compound 11

Intermediate 3 and 4-ethyl benzoyl chloride were used as raw materials, and operations were performed as they were in Example 1, to get white solid product (Compound 11).

$^1$H-NMR(400MHz,DMSO)δppm:10.54(1H,s),8.20(1H,d,J=8.0Hz),7.98(2H,d,J=8.0Hz),7.90(2H,d,J=8.0Hz),7.82 (2H,d,J=9.2Hz),7.40(2H,d,J=8.0Hz),4.38(1H,m),4.23(1H, m),4.10(1H,m),2.20(2H,m),2.13(1H,m),1.82(1H, m);EI-MS (m/z):389.3[M+H]$^+$.

Example 12

(S)-4-bromo-N-(4-(N-(2-oxotetrahydrofuran-3-yl) sulfamoyl)phenyl)benzamide (Compound 12)

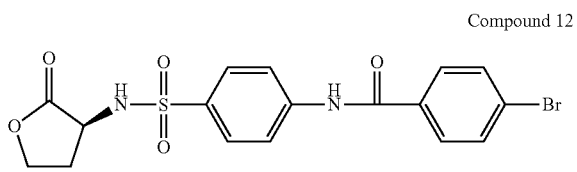 [SMILES: O=C(Nc1ccc(S(=O)(=O)N[C@H]2CCOC2=O)cc1)c1ccc(Br)cc1]

Compound 12

Intermediate 3 and 4-bromobenzoyl chloride were used as raw materials, and operations were performed as they were in Example 1, to get white solid product (compound 12).

$^1$H-NMR(400MHz,DMSO)δppm:10.68(1H,s),8.20(1H,d,J=8.0Hz),7.93(4H,m),7.94(4H,m),7.40(2H,d,J=8.0Hz),4.38 (1H,m),4.23(1H,m),4.09(1H,m),2.13(1H,m),1.83(1H,m); EI-MS(m/z):439.3[M+H]$^+$;m.p.112-113° C.

Example 13

(S)-4-propyl-N-(4-(N-(2-oxotetrahydrofuran-3-yl) sulfamoyl)phenyl)benzamide (Compound 13)

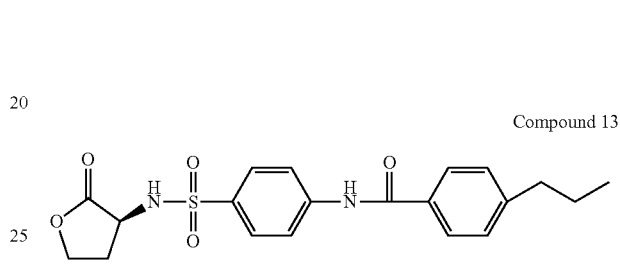

Compound 13

Intermediate 3 and 4-propyl benzoyl chloride were used as raw materials, and operations were performed as they were in Example 1, to get white solid product (Compound 13).

$^1$H-NMR(400MHz,DMSO)δppm:10.54(1H,s),8.20(1H,d,J=8.0Hz),8.00(2H,d,J=9.2Hz),7.90(2H,d,J=8.0Hz),7.82 (2H,d,J=9.6Hz),7.38(2H,d,J=9.2Hz),4.38(1H,m),4.23(1H, m),4.10(1H,m),2.66(2H,t,J=8.0Hz,J=8.0Hz),2.14(1H, m),1.83(1H,m),1.63(2H,m),0.91(3H,t,J=8.0Hz,J=8.0Hz); EI-MS(m/z):403.5[M+H]$^+$;m.p.247-249° C.

Example 14

(S)-4-chloro-N-(4-(N-(2-oxotetrahydrofuran-3-yl) sulfamoyl)phenyl)benzamide (Compound 14)

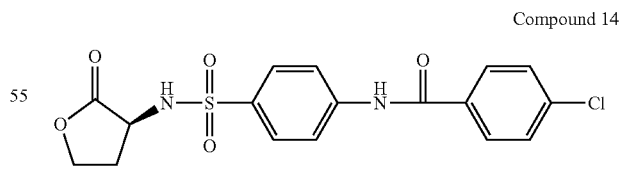

Compound 14

Intermediate 3 and 4-chlorobenzoyl chloride were used as raw materials, and operations were performed as they were in Example 1, to get white solid product (compound 14).

$^1$H-NMR(400MHz,DMSO)δppm:10.67(1H,s),8.20(1H,d,J=8.0Hz),7.99(4H,m),7.84(4H,d,J=9.2Hz),7.65(2H,d, J=8.4Hz),4.38(1H,m),4.23(1H,m),4.10(1H,m),2.13(1H,m), 1.83(1H,m);EI-MS(m/z):395.2[M+H]$^+$.

Example 15

(S)-4-(chloromethyl)-N-(4-(N-(2-oxotetrahydro-furan-3-yl)sulfamoyl)phenyl)benzamide (Compound 15)

Compound 15

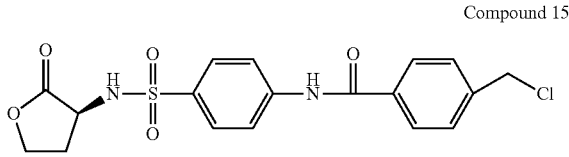 [SMILES: O=C(Nc1ccc(S(=O)(=O)N[C@H]2CCOC2=O)cc1)c1ccc(CCl)cc1]

Intermediate 3 and 4-(chloromethyl)benzoyl chloride were used as raw materials, and operations were performed as they were in Example 1, to get white solid product (compound 15).
$^1$H-NMR(400MHz,DMSO)δppm:10.64(1H,s),8.20(1H,d,J=8.0Hz),8.00(4H,m),7.84(2H,d,J=8.0Hz),7.63(2H,d,J=8.0Hz),4.86(2H,s),4.39(1H,s),4.23(1H,m),4.10(1H,m),2.13(1H,m),1.83(1H,m);EI-MS(m/z):409.2[M+H]$^+$; m.p.251-253° C.

Example 16

(S)-4-(tert-butyl)-N-(4-(N-(2-oxotetrahydrofuran-3-yl)sulfamoyl)phenyl)benzamide (Compound 16)

Compound 16

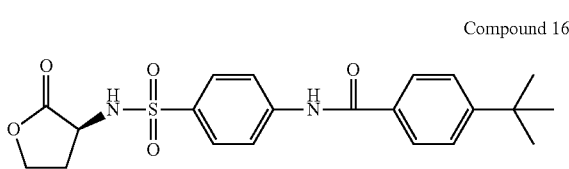 [SMILES: CC(C)(C)c1ccc(C(=O)Nc2ccc(S(=O)(=O)N[C@H]3CCOC3=O)cc2)cc1]

Intermediate 3 and 4-(tertbutyl)benzoyl chloride were used as raw materials, and operations were performed as they were in Example 1, to get white solid product (compound 16).
$^1$H-NMR(400MHz,DMSO)δppm:10.59(1H,s),8.25(1H,s),8.02(2H,d,J=8.0Hz),7.90(4H,m),7.58(2H,d,J=8.0Hz),4.36(1H,s),4.20(1H,s),4.10(1H,m),2.13(1H,m),1.83(1H,m),1.32(9H,s);EI-MS(m/z):417.4[M+H]$^+$;m.p.207-208° C.

Example 17

(S)-4-fluoro-N-(4-(N-(2-oxotetrahydrofuran-3-yl)sulfamoyl)phenyl)benzamide (Compound 17)

Compound 17

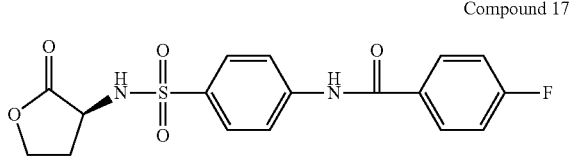 [SMILES: O=C(Nc1ccc(S(=O)(=O)N[C@H]2CCOC2=O)cc1)c1ccc(F)cc1]

Intermediate 3 and 4-fluorobenzoyl chloride were used as raw materials, and operations were performed as they were in Example 1, to get white solid product (compound 17).
$^1$H-NMR(400MHz,DMSO)δppm:10.63(1H,s),8.23(1H,d,J=8.0Hz),8.05(4H,m),7.83(2H,d,J=8.0Hz),7.40(2H,t,J=9.2Hz,J=8.4Hz),4.38(1H,m),4.23(1H,m),4.12(1H m),2.13(1H,m),1.83(1H,m);EI-MS(m/z):379.3[M+H]$^+$; m.p.236-237° C.

Example 18

(S)-4-cyano-N-(4-(N-(2-oxotetrahydrofuran-3-yl)sulfamoyl)phenyl)benzamide (Compound 18)

Compound 18

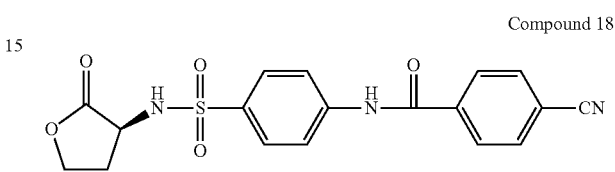

Intermediate 3 and 4-cyanobenzoyl chloride were used as raw materials, and operations were performed as they were in Example 1, to get white solid product (compound 18).
$^1$H-NMR(400MHz,DMSO)δppm:10.84(1H,s),8.23(1H,d,J=8.0Hz),8.11(4H,m),7.98(2H,d,J=8.0Hz),7.85(2H,d,J=8.0Hz),4.39(1H,m),4.23(1H,m),4.09(1H,m),2.15(1H,m),1.84(1H,m);EI-MS(m/z):386.3[M+H]$^+$;m.p.230-231° C.

Example 19

(S)-N-(4-(N-(2-oxotetrahydrofuran-3-yl)sulfamoyl)phenyl)-2-Phenylacetamide (Compound 19)

Compound 19

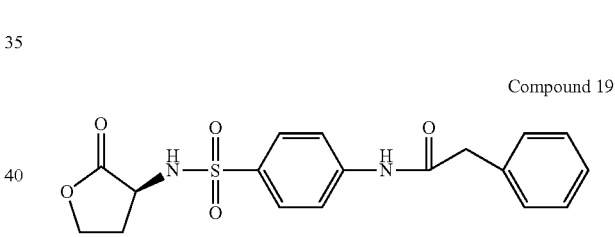

Intermediate 3 and phenylacetyl chloride were used as raw materials, and operations were performed as they were in Example 1, to get white solid product (compound 19).
$^1$H-NMR(400MHz,DMSO)δppm:10.57(1H,s),8.18(1H,d,J=8.8Hz),7.77(4H,m),7.33(5H,m),4.34(2H,m),4.20(1H,m),4.07(1H,m),3.68(2H,m),2.09(1H,m),1.79(1H,m);EI-MS(m/z): 375.3[M+H]$^+$;m.p.157-158° C.

Example 20

(S)-3-methyl-N-(4-(N-(2-oxotetrahydrofuran-3-yl)sulfamoyl)phenyl)benzamide (Compound 20)

Compound 20

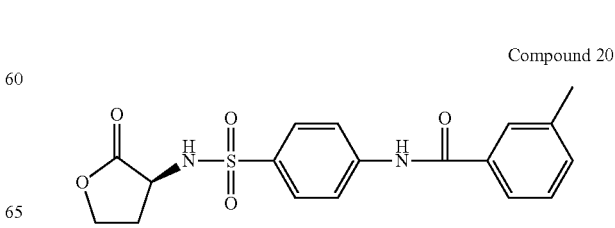

Intermediate 3 and 3-methyl benzoyl chloride were used as raw materials, and operations were performed as they were in Example 1, to get white solid product (compound 20).

¹H-NMR(400MHz,DMSO)δppm:10.59(1H,s),8.21(1H,d,J=8.0Hz),8.01(2H,d,J=8.0Hz),7.81(4H,m),7.45(2H,d,J=5.2Hz),4.39(1H,m),4.24(1H,m),4.11(1H,m), 2.41(3H,s),2.14(1H,m),1.84(1H,m);EI-MS(m/z):375.3[M+H]⁺; m.p.193-194° C.

Example 21

(S)-4-methoxyl-N-(4-(N-(2-oxotetrahydrofuran-3-yl)sulfamoyl)phenyl)benzamide (Compound 21)

Compound 21

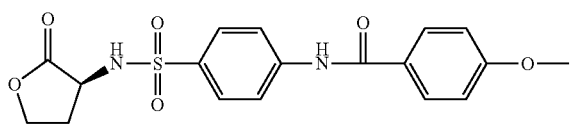

Intermediate 3 and 4-methoxyl benzoyl chloride were used as raw materials, and operations were performed as they were in Example 1, to get white solid product (compound 21).

¹H-NMR(400MHz,DMSO)δppm:10.45(1H,s),8.21(1H,d,J=9.2Hz),7.97(4H,m),7.81(2H,m),7.08(2H,d,J=8.0Hz),4.38(1H,m),4.23(1H,m),4.11(1H,m),2.13(1H,m),1.83(1H,m); EI-MS(m/z):391.2[M+H]⁺.

Example 22

(S)-3-chloro-N-(4-(N-(2-oxotetrahydrofuran-3-yl)sulfamoyl)phenyl)benzamide (Compound 22)

Compound 22

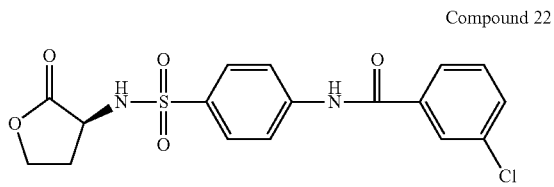 [SMILES: O=C(Nc1ccc(S(=O)(=O)N[C@H]2CCOC2=O)cc1)c1cccc(Cl)c1]

Intermediate 3 and 3-chlorobenzoyl chloride were used as raw materials, and operations were performed as they were in Example 1, to get white solid product (Compound 22).

¹H-NMR(400MHz,DMSO)δppm:10.74(1H,s),8.25(1H,d,J=8.8Hz),8.00(6H,m),7.71(1H,m),7.60(1H,m),4.38(1H,m),4.23(1H,m),4.11(1H,m),2.13(1H,m),1.83(1H,m);EI-MS(m/z): 395.3[M+H]⁺;m.p.213-214° C.; [α]$_D^{25}$=+10.4° (c=0.10, CH₃OH).

Example 23

(S)-3-fluoro-N-(4-(N-(2-oxotetrahydrofuran-3-yl)sulfamoyl)phenyl)benzamide (Compound 23)

Compound 23

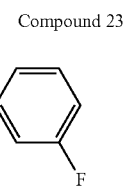

Intermediate 3 and 3-fluorobenzoyl chloride were used as raw materials, and operations were performed as they were in Example 1, to get white solid product (compound 23).

¹H-NMR(400MHz,DMSO)δppm:10.67(1H,s),8.24(1H,d,J=8.8Hz),8.00(2H,d,J=8.0Hz),7.82(4H,m),7.62(1H,m),7.50(1H,m),4.39(1H,m),4.23(1H,m),4.11(1H,m),2.15(1H,m),1.83(1H,m);EI-MS(m/z):379.2[M+H]⁺;m.p.201-203° C.; [α]$_D^{25}$=+9.3° (c=0.11,CH₃OH).

Example 24

(S)-2-fluoro-N-(4-(N-(2-oxotetrahydrofuran-3-yl)sulfamoyl)phenyl)benzamide (Compound 24)

Compound 24

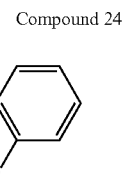

Intermediate 3 and 2-fluorobenzoyl chloride were used as raw materials, and operations were performed as they were in Example 1, to get white solid product (compound 24).

¹H-NMR(400MHz,DMSO)δppm:10.84(1H,s),8.24(1H,d,J=8.4Hz),7.93(2H,d,J=8.0Hz),7.83(2H,d,J=8.8Hz),7.69(1H,m),7.60(1H,m),4.38(1H,m),4.23(1H,m),4.10(1H,m),2.14(1H,m),1.83(1H,m);EI-MS(m/z):379.4[M+H]⁺; 205-207° C., [α]$_D^{25}$=+11.7° (c=0.12, CH₃OH).

Example 25

(S)-2-ethyoxyl-N-(4-(N-(2-oxotetrahydrofuran-3-yl)sulfamoyl)phenyl)benz amide (Compound 25)

Compound 25

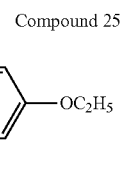

Intermediate 3 and 4-ethoxyl benzoyl chloride were used as raw materials, and operations were performed as they were in Example 1, to get white solid product (compound 25).

$^1$H-NMR(400MHz,DMSO)δppm:10.45(1H,s),8.20(1H,d,J=8.0Hz),7.97(4H,m),7.82(2H,d,J=8.0Hz),7.06(2H,d,J=8.0Hz),4.39(1H,m),4.24(1H,m),4.12(3H,m),2.14(1H,m),1.84(1H,m),1.36(3H,t,J=8.0Hz,J=8.0Hz);EI-MS(m/z): 405.3[M+H]$^+$;m.p. 256-258° C.

Example 26

(S)-4-nitro-N-(4-(N-(2-oxotetrahydrofuran-3-yl)sulfamoyl)phenyl)benzamide (Compound 26)

Compound 26

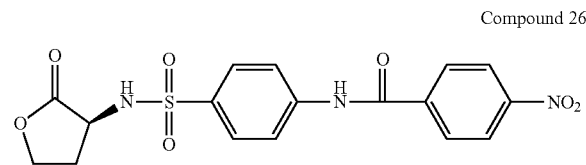 [SMILES: O=C(Nc1ccc(S(=O)(=O)N[C@H]2CCOC2=O)cc1)c1ccc([N+](=O)[O-])cc1]

Intermediate 3 and 4-nitrobenzoyl chloride were used as raw materials, and operations were performed as they were in Example 1, to get white solid product.
$^1$H-NMR(400MHz,DMSO)δppm:10.92(1H,s),8.41(1H,d,J=8.0Hz),8.21(3H,m),7.99(2H,d,J=8.0Hz),7.86(2H,d,J=8.0Hz),4.39(1H,m),4.24(1H,m),4.11(1H,m),2.16(1H,m),1.84(1H,m);EI-MS(m/z):406.2[M+H]$^+$;m.p.257-258° C.

Example 27

(S)-2-trifluoromethyl-N-(4-(N-(2-oxotetrahydrofuran-3-yl)sulfamoyl)phenyl)benzamide (Compound 27)

Compound 27

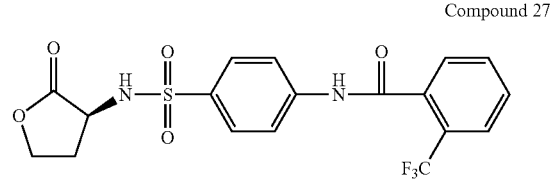 [SMILES: O=C(Nc1ccc(S(=O)(=O)N[C@H]2CCOC2=O)cc1)c1ccccc1C(F)(F)F]

Intermediate 3 and 2-trifluoromethyl benzoyl chloride were used as raw materials, and operations were performed as they were in Example 1, to get white solid product (compound 27).
$^1$H-NMR(400MHz,DMSO)δppm:10.99(1H,s),8.26(1H,d,J=8.0Hz),7.88(6H,m),7.77(2H,m),4.39(1H,m),4.24(1H,m),4.11(1H,m),2.17(1H,m),1.85(1H,m);EI-MS(m/z):429.4[M+H]$^+$;m.p.186-187° C.; $[α]_D^{25}$=+11.2° (c=0.10,CH$_3$OH).

Example 28

(S)-2-chloro-N-(4-(N-(2-oxotetrahydrofuran-3-yl)sulfamoyl)phenyl)benzamide (Compound 28)

Compound 28

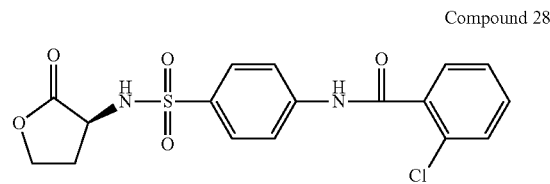

Intermediate 3 and 2-chlorobenzoyl chloride were used as raw materials, and operations were performed as they were in Example 1, to get white solid product (compound 28).
$^1$H-NMR(400MHz,DMSO)δppm:10.93(1H,s),8.25(1H,d,J=8.0Hz),7.92(2H,d,J=8.0Hz),7.84(2H,d,J=8.0Hz),7.59(4H,m),4.38(1H,m),4.24(1H,m),4.11(1H,m),2.15(1H,m),1.84(1H,m);EI-MS(m/z):395.2[M+H]$^+$;m.p.204-205° C.

Example 29

(D)-2-fluoro-N-(4-(N-(2-oxotetrahydrofuran-3-yl)sulfamoyl)phenyl)benzamide (Compound 29)

Compound 29

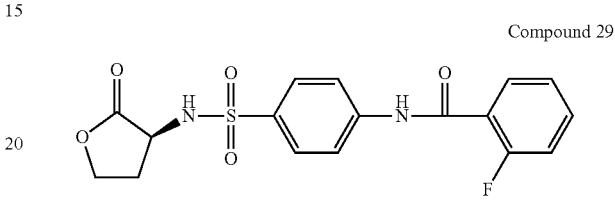

D-methionine was used as raw materials to synthesize (D)-4-amino-N-(2-oxotetrahydrofuran-3-yl)benzenesulfonamide by reference to the synthesis method of intermediates, 2-chlorobenzoyl chloride was used as raw materials, and operations were performed as they were in Example 1, to get white solid product (compound 29).
$^1$H-NMR(400MHz,DMSO)δppm:10.84(1H,s),8.24(1H,d,J=8.4Hz),7.93(2H,d,J=8.0Hz),7.83(2H,d,J=8.8Hz),7.69(1H,m),7.60(1H,m),4.38(1H,m),4.23(1H,m),4.10(1H,m),2.14(1H,m),1.83(1H,m);EI-MS(m/z):379.4[M+H]$^+$; 204-207° C., $[α]_D^{25}$=−6.7° (c=0.12, CH$_3$OH).

Experimental Example

EVALUATION OF ACTIVITY OF THE BACTERIAL QUORUM-SENSING REGULATORS ACCORDING TO THE INVENTION

The activity of the bacterial quorum-sensing regulators according to the invention may be measured by the following methods.

1. Method for Preliminary Screening 1.1 Preparation work: different compounds to be tested (Compounds 1-29 prepared in Example 1-29 and intermediates 1-3) were weighted and then were dissolved in 200 μl DMSO (dimethyl sulfoxide) to prepare a solution at a concentration of 0.065M. 5.0 mg inducer, N-hexanoyl homoserine lactone (C$_6$-HSL, purchased from Sigma Company), was weighted and was dissolved in 200 μl DMSO (at a concentration of 0.125M), and the compounds and the inducer were stored at 4□ for further use. C. violaceum CV026 (donated by Professor McLean J C from Texas State University) in LB culture medium (LB culture medium consisting of 1% (percentage by mass) tryptone, 0.5% (percentage by mass) yeast extract, 1% (percentage by mass) NaCl and water) was cultured under shaking in a shaker at 30□, 200 rpm to get the culture medium for further use.

1.2 Method for preliminary screening of compounds having agonistic activity: 400 μl C. violaceum CV026 (at a bacterial concentration of 1×10$^8$/ml) was added to 5 ml melted semi-solid LB culture medium, and was mixed well; the mixed culture medium was poured into a solid LB plate; when the mixed culture medium was solidified on the plate, lattice was made thereon; 1 μl of the dissolved compounds to be tested (Compounds 1-29 in Examples 1-29, at a concentration of 0.065M) was spotted on the plate; when the compounds on the plate was dried in air, the plate was put in a 30° C. oven upside down and was cultured for a period of 16-18 h. If the compound to be tested has an agonistic effect on *C. violaceum* CV026 on the LB plate, purple stain will be induced on the LB plate. The agonistic activity of a compound is determined depending on whether purple stain is induced for *C. violaceum* CV026 on LB plate as well as the purple depth.

1.3 Method for preliminary screening of compounds having inhibitory activity: the inducer $C_6$—HSL was diluted gradiently to 1000 times by means of 2-fold dilution; 15 µl diluted inducer and 400 µl *C. violaceum* CV026 in exponential phase (at a bacterial concentration of $1 \times 10^8$/ml) were mixed well and then were added to a 5 ml melted semi-solid LB culture medium; the mixture of inducer, *C. violaceum*, and semi-solid LB was poured onto a solid LB plate; when the mixture was solidified on the plate, lattice was made thereon; 1 µl of the dissolved compounds to be tested (Compounds 1-29 prepared in Example 1-29 and intermediates 1-3, at a concentration of 0.065M) was spotted on the plate; when the compounds on the plate were dried in air, the plate was put in a 30° C. oven upside down and was cultured for a period of 16-18 h. If the compound to be tested has an inhibitory effect on *C. violaceum* CV026 on the LB plate, white circle will appear on the LB plate. The inhibitory activity of a compound is preliminary determined depending on the size of the white circle appeared after *C. violaceum* CV026 was inhibited on LB plate.

It is found after preliminary screening that 20 compounds according to the invention have bacterial quorum sensing regulatory activity, and the screening result was shown in Table 1.

2. Measurement of $IC_{50}$ of Compounds Having an Inhibitory Effect on *C. violaceum* Quorum Sensing 2.1 The wells of a 12-well plate were marked as initial concentration, 2, 4, 8, 16, 32, 64, 128, 256, DMSO group, and a blank control group from left to right and from up to bottom, respectively.

2.2 The monoclonal *C. violaceum* CV026 grew on LB solid plate was cultured to exponational phase in a 5 ml fresh LB liquid culture medium, 50 µl was then taken for seeding in a 5 ml LB culture medium, and was cultured until the optical density OD value was about 1.0 at 585 nm; the culture was then mixed well with LB culture medium at a ratio of 1:9 by volume (with OD of about 0.15), and was added to a 12-well plate in an amount of 2 ml/well.

2.3 The compounds preliminarily screened to have quorum sensing inhibitory activity were dissolved respectively in DMSO (at a concentration of 0.065M), and then 10 µl was taken into 10 µl DMSO solution to achieve the purpose of 2-fold dilution, and so on. Each compound was gradiently diluted to a highest fold of 256 (gradient dilution of 2, 4, 8, 16, 32, 64, 128, 256 fold).

2.4 To each well, 15 µl 1000-fold diluted inducer $C_6$—HSL (initial concentration of 0.125M) and 8 µl compound solution at each diluted gradient was added; to DMSO control group, 8 µl DMSO was added; to a blank control group, 8 µl LB culture medium was added. Finally, it was ensured that 2 ml culture in each of the 12-well plate was mixed well.

2.5 The 12-well plate was placed in a 30° C. shaker at 130 rpm and was cultured for 10-12 h.

2.6 After the culture was finished, 1 ml culture was taken from each well and was put in a 1.5 ml EP tube and then was centrifuged at 12000 rpm for 10 mins. The supernatant of the culture was sucked out, and 500 µl DMSO was added to each EP tube to dissolve the purple pigment in the culture. After the pigment was completely dissolved, centrifugation was performed at 12000 rpm for 10 mins. 200 µl supernatant pigment was put in a 96-well culture plate, and was measured for absorbance value at 585 nm by a Microplate Reader, and the absorbance value was measured at 585 nm by a microplate reader, the absorbance value and the corresponding concentration were plotted to get the $IC_{50}$ value. The specific results are shown in Table 2.

TABLE 1

Screening result of bacterial quorum sensing regulatory activity

| Compound No. | Regulatory activity | Compound No. | Regulatory activity |
| --- | --- | --- | --- |
| Intermediate 1 | + | Intermediate 2 | − |
| 1 | − | 2 | − |
| 3 | − | 4 | − |
| 5 | − | 6 | − |
| 9 | − | 12 | ± |
| 14 | − | 15 | + |
| 16 | − | 17 | − |
| 20 | − | 22 | − |
| 23 | − | 24 | − |
| 27 | − | 28 | − |

In Table 1, "+" represents that a compound has bacterial quorum sensing agonistic activity, "−" represents that a compound has bacterial quorum sensing inhibitory activity, and "±" represents that a compound has both agonistic and inhibitory activity on the bacterial quorum sensing.

TABLE 2

$IC_{50}$ value (µM) of compounds having bacterial quorum sensing inhibitory activity

| Compound No. | $IC_{50}$ | Compound No. | $IC_{50}$ |
| --- | --- | --- | --- |
| 4 | 29.00 ± 2.41 | 9 | 17.25 ± 2.60 |
| 17 | 14.72 ± 2.58 | 23 | 7.79 ± 2.68 |
| 24 | 1.64 ± 0.27 | 27 | 4.91 ± 0.97 |
| 28 | 1.66 ± 0.33 | | |

The experiments on evaluation of activity of said bacterial quorum-sensing regulators demonstrated that compounds of Formula I according to the invention, particularly Compound 1-6, 9, 12, 14-17, 20, 22-24 and 27-28 had a regulatory effect on bacterial quorum sensing, wherein Compound 1-6, 9, 14, 16, 17, 20, 22-24, 27-28 had an inhibitory effect on bacterial quorum sensing, while Compound 15 had an agonizing effect on bacterial quorum sensing, and Compound 12 had both an agonizing effect and an inhibitory effect on bacterial quorum sensing.

To sum up, the invention synthesizes a class of new bacterial quorum-sensing regulators represented by Formula I, which do not interfere with normal physiological functions of cells in vivo, and thus are regarded as new direction for the development of antibacterials, wherein the bacterial quorum-sensing inhibitors can be used in combination with antibiotics, to treat an infection or a disease (including, but not limited to peritonitis, cholecystitis, cystitis, diarrhea, endocarditis, gastroenteritis, pyothorax, sepsis and other various diseases) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shi-* gella spp., *Pasteurella, Vibrio cholerae*, and *Vibrio Parahemolyticus*, particularly, a disease caused by drug-resistant Gram-negative bacteria not sensitive to current antibiotics.

What is claimed is:

1. A derivative of homoserine lactone represented by formula I, a racemate or optical isomer, a pharmaceutically acceptable salt, a solvate or a hydrate thereof,

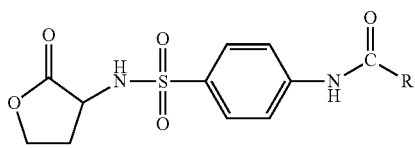

wherein
R is C1-12 linear or branched alkyl, or phenyl, said alkyl or phenyl is optionally mono-substituted or multi-substituted by a substituent selected from the group consisting of: (a) phenyl, (b) substituted or unsubstituted C1-5 linear or branched alkyl, (c) halogen, (d) cyano, (e) trifluoromethyl, (f) hydroxyl, (g) nitro, and (h) substituted or unsubstituted C1-5 alkoxyl.

2. The derivative of homoserine lactone represented by formula I, a racemate or optical isomer, a pharmaceutically acceptable salt, a solvate or a hydrate thereof according to claim 1, wherein R is C1-9 linear or branched alkyl, or phenyl, said alkyl or phenyl is optionally mono-substituted or multi-substituted by a substituent selected from the group consisting of: (a) phenyl, (b) C1-5 linear or branched alkyl, (c) C1-5 linear or branched alkyl mono-substituted or multi-substituted by halogen, (d) halogen, (e) cyano, (f)trifluoromethyl, hydroxyl, (g) nitro,(h) C1-5 alkoxyl, and (i) C1-5 alkoxyl mono-substituted or multi-substituted by halogen.

3. The derivative of homoserine lactone represented by formula I, a racemate or optical isomer, a pharmaceutically acceptable salt, a solvate or a hydrate thereof according to claim 1, selected from the following group consisting of:
(S)-N-(4-(N-(2-oxotetrahydrofuran-3-yl)sulfamoyl)phenyl)propanamide (Compound 1),
(S)-N-(4-(N-(2-oxotetrahydrofuran-3-yl)sulfamoyl)phenyl)butyrylamide (Compound 2),
(S)-N-(4-(N-(2-oxotetrahydrofuran-3-yl)sulfamoyl)phenyl)pentanamide (Compound 3),
(S)-N-(4-(N-(2-oxotetrahydrofuran-3-yl)sulfamoyl)phenyl)hexanamide (Compound 4),
(S)-N-(4-(N-(2-oxotetrahydrofuran-3-yl)sulfamoyl)phenyl)heptanamide (Compound 5),
(S)-N-(4-(N-(2-oxotetrahydrofuran-3-yl)sulfamoyl)phenyl)octanamide (Compound 6),
(S)-N-(4-(N-(2-oxotetrahydrofuran-3-yl)sulfamoyl)phenyl)pelargonamide (Compound7),
(S)-N-(4-(N-(2-oxotetrahydrofuran-3-yl)sulfamoyl)phenyl)decanamide (Compound 8),
(S)-N-(4-(N-(2-oxotetrahydrofuran-3-yl)sulfamoyl)phenyl)benzamide (Compound 9),
(S)-4-methyl-N-(4-N-(2-oxotetrahydrofuran-3-yl)sulfamoyl)phenyl) benzamide (Compound 10),
(S)-4-ethyl-N-(4-(N-(2-oxotetrahydrofuran-3-yl)sulfamoyl)phenyl)benzamide (Compound 11),
(S)-4-bromo-N-(4-(N-(2-oxotetrahydrofuran-3-yl)sulfamoyl)phenyl)benzamide (Compound 12),
(S)-4-propyl-N-(4-(N-(2-oxotetrahydrofuran-3yl)sulfamoyl)phenyl)benzamide (Compound 13),
(S)-4-chloro-N-(4-(N-(2-oxotetrahydrofuran-3yl)sulfamoyl)phenyl)benzamide (Compound 14),
(S)-4-(chloromethyl)-N-(4-(N-(2-oxotetrahydrofuran-3-yl)sulfamoyl)phenyl)benzamide (Compound 15),
(S)-4-(tert-butyl)-N-(4-(N-(2oxotetrahydrofuran-3-yl)sulfamoyl)phenyl)benzamide (Compound 16),
(S)-4-fluoro-N-(4-(N-(2-oxotetrahydrofuran-3-yl)sulfamoyl)phenyl)benzamide (Compound 17),
(S)-4-cyano-N-(4-(N-(2-oxotetrahydrofuran-3-yl)sulfamoyl)phenyl)benzamide (Compound 18),
(S)-N-(4-(N-(2-oxotetrahydrofuran-3-yl)sulfamoyl)phenyl)phenylacetamide (Compound 19),
(S)-3-methyl-N-(4-(N-(2-oxotetrahydrofuran-3-yl)sulfamoyl)phenyl)benzamide (Compound 20),
(S)-4-methoxyl-N-(4-(N-(2-oxotetrahydrofuran-3-yl)sulfamoyl)phenyl)benzamide (Compound 21),
(S)-3-chloro-N-(4-(N-(2-oxotetrahydrofuran-3-yl)sulfamoyl)phenyl)benzamide (Compound 22),
(S)-3-fluoro-N-(4-(N-(2-oxotetrahydrofuran-3-yl)sulfamoyl)phenyl)benzamide (Compound 23),
(S)-2-fluoro-N-(4-(N-(2-oxotetrahydrofuran-3-yl)sulfamoyl)phenyl)benzamide (Compound 24),
(S)-2-ethyoxyl-N-(4-(N-(2-oxotetrahydrofuran-3-yl)sulfamoyl)phenyl)benzamide (Compound 25),
(S)-4-nitryl-N-(4-(N-(2-oxotetrahydrofuran-3-yl)sulfamoyl)phenyl)benzamide (Compound 26),
(S)-2-trifluoromethyl-N-(4-(N-(2-oxotetrahydrofuran-3-yl)sulfamoyl)phenyl)benzamide (Compound 27),
(S)-2-chloro-N-(4-(N-(2-oxotetrahydrofuran-3-yl)sulfamoyl)phenyl)benzamide (Compound 28), and
(D)-2-fluoro-N-(4-(N-(2-oxotetrahydrofuran-3-yl)sulfamoyl)phenyl)benzamide (Compound 29).

4. The derivative of homoserine lactone represented by formula I, a racemate or optical isomer, a pharmaceutically acceptable salt, a solvate or a hydrate thereof according to claim 1, selected from the following group consisting of:
(S)-N-(4-(N-(2-oxotetrahydrofuran-3-yl)sulfamoyl)phenyl)propanamide (Compound 1),
(S)-N-(4-(N-(2-oxotetrahydrofuran-3-yl)sulfamoyl)phenyl)butyrylamide (Compound 2),
(S)-N-(4-(N-(2-oxotetrahydrofuran-3-yl)sulfamoyl)phenyl)pentanamide (Compound 3),
(S)-N-(4-(N-(2-oxotetrahydrofuran-3-yl)sulfamoyl)phenyl)hexanamide (Compound 4),
(S)-N-(4-(N-(2-oxotetrahydrofuran-3-yl)sulfamoyl)phenyl)heptanamide (Compound 5),
(S)-N-(4-(N-(2-oxotetrahydrofuran-3-yl)sulfamoyl)phenyl)octanamide (Compound 6),
(S)-N-(4-(N-(2-oxotetrahydrofuran-3-yl)sulfamoyl)phenyl)benzamide (Compound 9),
(S)-4-bromo-N-(4-(N-(2-oxotetrahydrofuran-3-yl)sulfamoyl)phenyl)benzamide (Compound 12),
(S)-4-chloro-N-(4-(N-(2-oxotetrahydrofuran-3-yl)sulfamoyl)phenyl)benzamide (Compound 14),
(S)-4-(tert-butyl)-N-(4-(N-(2-oxotetrahydrofuran-3-yl) sulfamoyl)phenyl)benzamide (Compound 16),
(S)-4-fluoro-N-(4-(N-(2-oxotetrahydrofuran-3-yl)sulfamoyl)phenyl)benzamide (Compound 17),
(S)-3-methyl-N-(4-(N-(2-oxotetrahydrofuran-3-yl)sulfamoyl)phenyl)benzamide (Compound 20),
(S)-3-chloro-N-(4-(N-(2-oxotetrahydrofuran-3-yl)sulfamoyl)phenyl)benzamide (Compound 22),
(S)-3-fluoro-N-(4-(N-(2-oxotetrahydrofuran-3-yl)sulfamoyl)phenyl)benzamide (Compound 23),
(S)-2-fluoro-N-(4-(N-(2-oxotetrahydrofuran-3-yl)sulfamoyl)phenyl)benzamide (Compound 24), (S)-2-trifluoromethyl-N-(4-(N-(2-oxotetrahydrofuran-3-yl)sulfamoyl)phenyl)benzamide (Compound 27), and
(S)-2-chloro-N-(4-(N-(2-oxotetrahydrofuran-3-yl)sulfamoyl)phenyl)benzamide (Compound 28).

5. The derivative of homoserine lactone represented by formula I, a racemate or optical isomer, a pharmaceutically acceptable salt, a solvate or a hydrate thereof according to claim 1, selected from the following group consisting of:
(S)-4-bromo-N-(4-(N-(2-oxotetrahydrofuran-3-yl)sulfamoyl)phenyl)benzamide (Compound 12), and
(S)-4-(chloromethyl)-N-(4-(N-(2-oxotetrahydrofuran-3-yl)sulfamoyl)phenyl) benzamide (Compound 15).

6. A method for preparing the derivative of homoserine lactone represented by formula I according to claim 1, comprising the following steps of: reacting an intermediate represent by formula 3 with acyl chloride represented by RCOCl, to prepare the derivative of homoserine lactone represented by formula I,

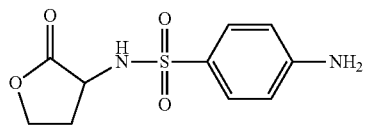

3 wherein R is C1-12 linear or branched alkyl, or phenyl, said alkyl or phenyl is optionally mono-substituted or multi-substituted by a substituent selected from the group consisting of: (a) phenyl, (b) substituted or unsubstituted C1-5 linear or branched alkyl, (c) halogen, (d) cyano, (e) trifluoromethyl, (f)hydroxyl, (g) nitro, and (h) substituted or unsubstituted C1-5 alkoxyl.

7. A pharmaceutical composition, comprising the derivative of homoserine lactone represented by formula I, the racemate or optical isomer, a pharmaceutically acceptable salt, a solvate or a hydrate thereof according to claim 1, and optionally one or more pharmaceutical acceptable carriers or excipients.

8. The derivative of homoserine lactone represented by formula I, a racemate or optical isomer, a pharmaceutically acceptable salt, a solvate or a hydrate thereof according to claim 1, wherein R is C1-9 linear or branched alkyl, or phenyl, said alkyl or phenyl is optionally mono-substituted or multi-substituted by a substituent selected from the group consisting of: (a) phenyl, (b) linear or branched C1-4 alkyl, (c) C1-4 linear or branched alkyl mono-substituted or multi-substituted by halogen, (d) halogen, (e) cyano, (f) trifluoromethyl, (g) hydroxyl, (h) nitro, (i) C1-4 alkoxyl, and (j) C1-4 alkoxy mono-substituted or multi-substituted by halogen.

9. The derivative of homoserine lactone represented by formula I, a racemate or optical isomer, a pharmaceutically acceptable salt, a solvate or a hydrate thereof according to claim 1, wherein R is methyl, ethyl, n-propyl, isopropyl, n-butyl, sec-butyl, tert-butyl, pentyl, hexyl, heptyl, octyl, nonyl, phenyl, chlorophenyl, bromophenyl, fluorophenyl, nitrophenyl, cyanophenyl, methylphenyl, ethylphenyl, benzyl, trifluoromethylphenyl, methoxyphenyl, ethoxyphenyl, or halogenated methylphenyl.

10. The method according to claim 6, wherein the intermediate represented by formula 3 is obtained by reacting acetamino-benzenesulfonyl chloride with homoserine lactone hydrobromide.

11. The pharmaceutical composition according to claim 7, wherein the pharmaceutical composition may further comprise one or more antibiotics.

12. A method for regulation of bacterial quorum sensing, the method comprising administering to bacteria an effective amount of at least one of the derivatives of homoserine lactone represented by formula I, a racemate or optical isomer, a pharmaceutically acceptable salt, a solvate or a hydrate thereof according to claim 1.

13. A method for inhibition of bacterial quorum sensing, the method comprising administering to bacteria an effective amount of at least one of the derivative of homoserine lactone represented by formula I, a racemate or optical isomer, a pharmaceutically acceptable salt, a solvate or a hydrate thereof according to claim 4.

14. A method for agonism of bacterial quorum sensing, the method comprising administering to bacteria an effective amount of at least one of the derivative of homoserine lactone represented by formula I, a racemate or optical isomer, a pharmaceutically acceptable salt, a solvate or a hydrate thereof according to claim 5.

* * * * *